(12) United States Patent
McGuire

(10) Patent No.: US 7,687,473 B2
(45) Date of Patent: Mar. 30, 2010

(54) 5-AMINO-4-IMIDAZOLECARBOXAMIDE RIBOSIDE AND ITS NUCLEOBASE AS POTENTIATORS OF ANTIFOLATE TRANSPORT AND METABOLISM

(75) Inventor: John J. McGuire, Kenmore, NY (US)

(73) Assignee: Health Research, Inc., Buffalo, NY (US)

( * ) Notice: Subject to any disclaimer, the term of this patent is extended or adjusted under 35 U.S.C. 154(b) by 1104 days.

(21) Appl. No.: 11/327,872

(22) Filed: Jan. 9, 2006

(65) Prior Publication Data

US 2006/0160751 A1    Jul. 20, 2006

Related U.S. Application Data

(60) Provisional application No. 60/642,063, filed on Jan. 7, 2005, provisional application No. 60/649,153, filed on Feb. 2, 2005.

(51) Int. Cl.
*A01N 43/04* (2006.01)
*A61K 31/70* (2006.01)

(52) U.S. Cl. .......................... 514/42; 514/43; 514/251; 514/400

(58) Field of Classification Search ....................... None
See application file for complete search history.

(56) References Cited

U.S. PATENT DOCUMENTS

| 4,912,092 | A | * | 3/1990 | Gruber ........................ 514/45 |
| 6,011,040 | A | | 1/2000 | Muller et al. |
| 6,184,227 | B1 | | 2/2001 | Karmali |
| 6,573,248 | B2 | | 6/2003 | Ramasamy et al. |

* cited by examiner

*Primary Examiner*—Traviss C McIntosh, III
(74) *Attorney, Agent, or Firm*—Hodgson Russ LLP

(57) ABSTRACT

The present invention provides a method for increasing the efficacy of antifolates which act via inhibition of dihydrofolate reductase (DHFR). The method comprises the steps of administration of 5-amino-4-imidazolecarboxamide riboside (Z) or its base with the antifolate such that the targeted cells are exposed to both the antifolate and Z simultaneously. This results in increased influx of the antifolate. For MTX, accumulation of the more biologically active polyglutamate forms is also potentiated. This potentiation appears to be mediated by an effect on the RFC.

17 Claims, 5 Drawing Sheets

5-AMINO-4-IMIDAZOLECARBOXAMIDE RIBOSIDE AND ITS NUCLEOBASE AS POTENTIATORS OF ANTIFOLATE TRANSPORT AND METABOLISM

This application claims priority to U.S. provisional application No. 60/642,063, filed on Jan. 7, 2005 and to U.S. provisional application No. 60/649,153, filed on Feb. 2, 2005, the disclosures of which are incorporated herein by reference.

This work was funded by Grant No. CA43500 from the National Cancer Institute. The Government has certain rights in the invention

BACKGROUND

Reduced folates are a family of vitamins that participate as cofactors in one-carbon transfer reactions that are involved in de novo synthesis of purines and thymidylate; synthesis of the amino acids serine, glycine, and methionine; degradation of histidine; scavenging of one-carbon metabolites such as formaldehyde and formate [1]. Folates themselves cannot be synthesized de novo by humans and thus must be obtained from dietary sources and by release from autotrophic enteric bacteria. Dietary and bacterially-derived folates are absorbed in the gut and transported as 5-methyltetrahydrofolate in the blood to the tissues. Once at the tissues, two general transport systems are available to cells for internalizing folates: (1) the folate-binding protein (FBP) family of endocytic, unidirectional, membrane receptor transporters; and (2) the reduced folate carrier (RFC; SLC19A1) carrier-mediated, bi-directional facilitated diffusion system [2].

Protein expression of these transporters is tissue-dependent. The RFC is expressed in most, if not all, tissues [3], while expression of the various FBP is limited to a few tissues [4]. Because of its wide distribution and its high capacity, the RFC is believed to be the primary means for transport of folates [2]. Of interest is that under most conditions, expression of the RFC is relatively constant in tissues in which it is expressed, although the levels expressed in different tissues vary widely. RFC activity may increase in acute folate deficiency [5], however; the mechanism of this increase is unknown. It has been suggested, based on the activation of human RFC promoter constructs by ectopic expression of specific transcription factors [6], that RFC expression could be transcriptionally regulated. However, data to support such regulation under physiological conditions is limited. Elucidation of mechanisms for regulating the transport of natural folates would be of fundamental interest.

Antifolates are antagonists of the action of the folate family of essential human vitamins, all of which are derived from the folic acid structure. The most commonly used antifolate in humans is currently methotrexate (MTX). However recently, two new antifolates with the same and/or different mechanisms of inhibiting folate metabolism have entered limited clinical use. These are raltitrexed (Tomudex; AstraZeneca) and pemetrexed (ALIMTA; Eli Lilly). MTX is used to treat a number of pathological conditions, including cancer, rheumatoid arthritis, psoriasis, and graft-versus-host-disease following bone marrow transplantation. The new antifolates are currently only approved to treat specific cancers (colon cancer and mesothelioma), but are undergoing clinical trial in tumors of other organ sites and in other diseases. A large number of antifolates have been made and tested preclinically; a number of these are now in clinical trial Antifolates that closely resemble the folates structurally and which include the single glutamate (Glu) moiety that occurs in folates are termed "classical" antifolates. Classical antifolates including methotrexate (MTX), ZD1694, and pemetrexed are primarily transported into human cells by the equilibrative reduced folate carrier (RFC) and/or FBP [7]. Transport by tumors can be limiting to the therapeutic effect of antifolates. Once transported, classical antifolates are metabolized by folylpolyglutamate synthetase (FPGS) to poly($\gamma$-glutamyl) forms, typically containing 1-7 additional glutamates in gamma-linkage. The polyglutamates are better retained within cells than are monoglutamates and provide a reservoir of drug that continues to act after extracellular drug declines or is removed. In addition, polyglutamyl antifolates may also be significantly more potent as inhibitors of their respective target enzymes.

Discovery of mechanisms by which antifolate transport could be increased in tumor cells might lead to greater therapeutic benefit from clinical use of current and future antifolates. In addition, metabolism of classical antifolates to their poly($\gamma$-glutamate) forms by folylpolyglutamate synthetase is often limited by transport. Since polyglutamyl antifolates are better retained and are often more potent inhibitors of their target enzyme than is the parent monoglutamate, increased transport could also lead to enhanced synthesis of these important metabolites. This could be especially critical in childhood acute lymphoblastic leukemia where clinical correlations have shown that the median difference in MTX polyglutamate (MTXGn) accumulation between patients who respond to MTX-containing therapy and those who do not respond is only about three-fold. Increasing uptake of MTX even three-fold could increase MTXGn synthesis and might thus increase the number of long-term survivors.

SUMMARY OF THE INVENTION

The present invention provides a method for enhancing the uptake and efficacy of antifolates which act via inhibition of DHFR such as the 2,4 diaminopteridine antifolates methotrexate and aminopterin.

The method is based on the unexpected observation that exogenous 5-amino-4-imidazolecarboxamide riboside (Z), a nucleoside precursor of (among others) the triphosphate ZTP, potentiates uptake of MTX and synthesis of MTX polyglutamate in cancer cells. Based on the data presented herein, it is considered that Z potentiates transport of antifolates via the RFC and the increased transport leads to increased synthesis of antifolate polyglutamates and consequently increased drug accumulation. Z was observed to enhance the growth inhibitory potency of MTX against cancer cells.

Thus in one embodiment, this invention provides a method comprising the administration of Z or its base (i.e., 5-amino-4-imidazolecarboxamide) with an antifolate which acts via inhibition of the DHFR at concentrations at which the antifolate inhibits DHFR. The administration of Z or its base can be accomplished by any standard method, although systemic administration is preferred. Z has already been tested in clinical trials as a treatment for cardiac ischemia and is known to be nontoxic.

In another embodiment, Z or its base and an antifolate which acts via inhibition of DHFR can be administered with a second antifolate(s) which primarily act via another mechanism such as inhibition of thymidylate synthase, inhibition of purine synthesis or other multi-targeted inhibition pathways.

Administration of Z or its base with folate(s) which inhibit DHFR (with or without other folates) to enhance the efficacy of the folate(s) can be carried out for inhibiting the growth of cells as in various cancers as well as in other pathological conditions such as rheumatoid arthritis and psoriasis.

DESCRIPTION OF THE INVENTION

Figure 1:
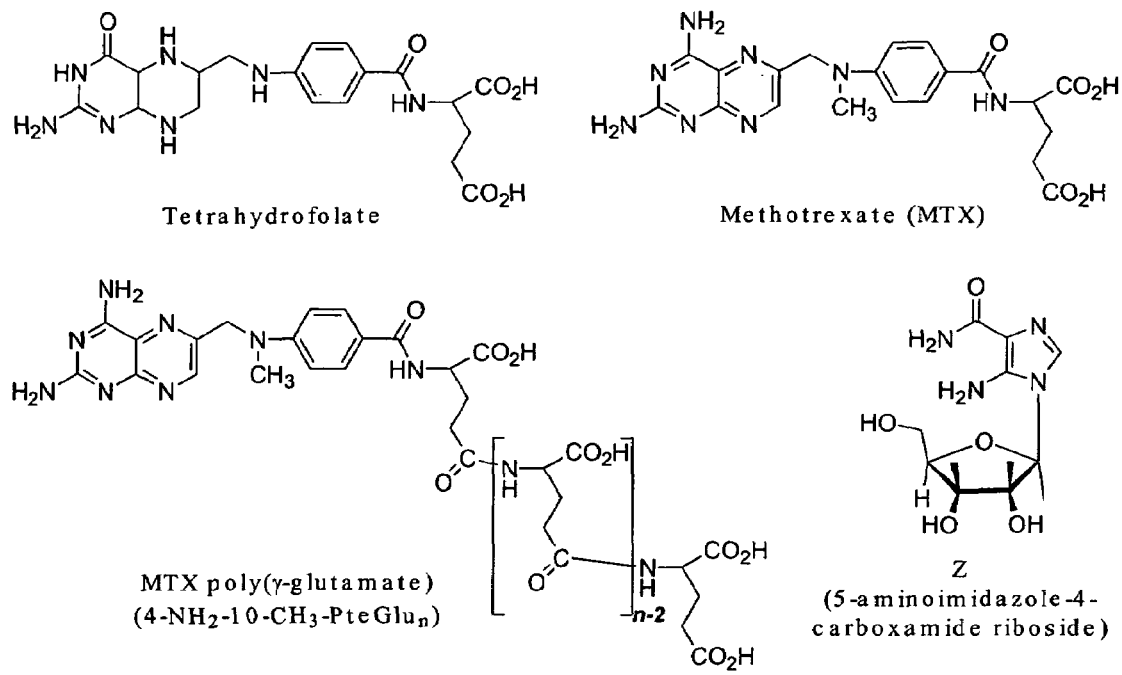
FIG. 1. Structures of tetrahydrofolate ($H_4$PteGlu), methotrexate (MTX), methotrexate poly(γ-glutamate) metabolites, and 5-aminoimidazole-4-carboxamide riboside (Z).

The abbreviations used are: ActD, Actinomycin D; AMPK, AMP-activated protein kinase; AMT, aminopterin (4-aminopteroylglutamic acid); BW1843U89, (S)-2-(5-(((1,2-dihydro-3-methyl-1-oxobenzo(F)quinazolin-9-yl)methyl)-amino)-1-oxo-2-isoindolinyl)glutaric acid; CHX, cycloheximide; DDATHF, 5,10-dideazatetrahydrofolate; DHFR, dihydrofolate reductase (EC 1.5.1.3); FPGS, folylpolyglutamate synthetase (EC 6.3.2.17); HBSS; HEPES-buffered balanced salt solution; MHS, anion-free buffer system containing 250 mM sucrose and 20 mM HEPES, titrated to pH 7.4 with MgO; LV, leucovorin ([6R,S]-5-formyltetrahydrofolate); MTX, methotrexate (4-amino-10-methylpteroylglutamic acid; 4-$NH_2$-10-$CH_3$-PteGlu); 4-$NH_2$-10-$CH_3$-PteGlu$_n$, MTX poly(γ-glutamyl metabolites) containing n total glutamates); NHS, N-hydroxysuccinimide; PteGlu, folic acid; TMPS, thymidylate synthase (EC 2.1.1.45); TMTX, trimetrexate; Z, 5-amino-4-imidazolecarboxamide riboside (AICAr); Z-base, 5-amino-4-imidazolecarboxamide; ZD1694, N-[5-[N-(3,4-dihydro-2-methyl-4-oxoquinazolin-6-ylmethyl)-N-methylamino]-2-thenoyl]-L-glutamic acid (raltitrexed; Tomudex).

The present invention provides a method for enhancing the uptake and efficacy of antifolates which act by inhibition of DHFR (referred to herein as a DHFR inhibitory antifolate). The potentiation effect of Z or its base is observed when the antifolate is used at a concentration at which it inhibits DHFR. The method comprises the steps of administering to an individual in need of treatment, an effective dose of Z or its base and the DHFR inhibitory antifolate at a concentration at which the antifolate inhibits DHFR.

The antifolates which act by inhibition of DHFR and are transported by RFC include, but are not limited to, pyridopyrimidine compounds such as methotrexate, aminopterin, and edetrexate (10-ethyl-10-deaaaminopterin). Also included are quinazoline, pyrrolopyrimidine, and furopyrimidine antifolates, generally containing a 2,4-diamino moiety, that inhibit DHFR. Also included are variants of such analogs that contain any structural feature (e.g., 7-methyl substitution and/or substitution of an amino acid analog for the glutamic acid analog inherent to so-called classical analogs of folic acid) that abrogates synthesis of poly(gamma-glutamyl) metabolites; an example would be gamma-fluoromethotrexate. It should be noted that pemetrexed, a so-called multi-targeted antifolate, primarily acts through inhibition of thymidylate synthase, although at higher levels it may also inhibit DHFR and GAR formyltransferase (Curtin N J, Hughes A N. Pemetrexed disodium, a novel antifolate with multiple targets. Lancet Oncol 2001; 2: 298-306). Thus in most cases (i.e., at concentrations at which it does not inhibit DHFR), pemetrexed is not an antifolate whose uptake or efficacy can be enhanced by Z without another antifolate which acts via inhibition of DHFR. However, at higher concentrations at which pemetrexed can inhibit DHFR, Z or its base may potentiate its uptake and efficacy.

Accordingly, this invention involves the use of 5-amino-4-imidazolecarboxamide riboside (AICA riboside—or Z), 5-amino-4-imidazolecarboxamide (AICA—or Z-base). It should be understood that the terms Z and Z-base include pharmaceutically acceptable salts thereof. The formula for Z is shown in FIG. 1. The compounds Z and Z-base are available commercially (Sigma Chemical Company, St. Louis, Mo.), or may be synthesized by conventional techniques of organic chemistry, for example, as described in U.S. Pat. No. 3,919,192 or in U.S. Pat. No. RE 34,387. Suitable salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, latate, maleate, methanesulfonate, 2-naphthalenesulfonate, nicotinate, oxalate, palmitate, pectinate, persulfate, 3-phenylpropionate, picrate, pivalate, propionate, succinate, tartrate, thiocyanate, tosylate, and undecanoate.

For the method of the present invention, Z or its base can be delivered to the target tissue by any means known to those skilled in the art. Although Z or its base could be administered orally, because its absorption is limited when administered via oral route, it is preferred that Z be administered systemically (including through intravenous, intradermal, intraperitoneal, intramuscular, or intra-tumoral, mucosal, topical and other similar routes). If given orally, it is preferable to provide it in formulations which would enhance its absorption and therefore delivery to the targeted tissues. To achieve a potentiating effect of Z or its base on the antifolate uptake, the targeted tissue or cells should be exposed to both Z and the antifolate at the same time. In one embodiment, Z is preferably present during the antifolate exposure. Accordingly, the invention comprises initiating the administration of Z prior to, simultaneously or following administration of one or more antifolates of interest such that the targeted tissues or cells are exposed to both agents. This can be conveniently achieved with the concurrent administration of both Z and the antifolate. The dose of Z used can vary from the highest practicable dose to the lowest dose achieving potentiation in vivo. These ranges can be determined empirically in a clinical setting by those skilled in the art. Generally, a dose of 0.1 mg/kg/hr to 200 mg/kg/hr can be used. Previously, in human ischemic heart disease trials a 30 min infusion of Z at 100 mg/kg was given (Dixon et al., J Clin Pharmacol 1991; 31(4): 342-70 and in an initial multicenter, randomized controlled trial on the safety and efficacy of acadesine in patients undergoing coronary artery bypass graft surgery (SPI Research Group), a 7 hr infusion of Z at a maximum dose of 0.38 mg/kg/min was given (Leung et al., Anesth Analg 1994 March; 78(3):420-34).

In clinical applications, MTX is generally given for childhood leukemias as intravenous infusion at a high dose to target malignant cells following which leucovorin is administered for rescue of normal cells. Thus, in one embodiment, Z and/or its base can be infused separately or together with a DHFR inhibitory antifolate for suitable periods of time such as between 6 to 36 hours. In a preferred embodiment, the infusion can be between 12-24 hours. As a follow up to the high dose of MTX, a lower dose is generally administered orally for maintenance purposes. Therefore, in this embodiment, Z and/or its base can also be administered as an infusion or orally during the period of DHFR inhibitory antifolate intake.

Data presented herein indicates that Z's potentiation of methotrexate efficacy is mediated via inhibition of DHFR. Although methotrexate is also considered to be a thymidylate synthase inhibitor, data presented in Example 2. indicates that inhibition of TMPS is not necessary for Z's potentiation of MTX uptake and efficacy. Similarly, inhibition of purine synthesis was not necessary (Example 3). In contrast, DHFR inhibition was sufficient as well as necessary for Z's potentiation of MTX uptake and efficacy. Further, because another antifolate which is an inhibitor of DHFR, aminopterin, also showed similar enhancement of MTX uptake, it is believed that Z will potentiate the uptake and efficacy of antifolates which act via inhibition of DHFR at concentrations at which DHFR is inhibited. Finally, the presence of a lipophilic DHFR inhibitor, trimetrexate, that does not use the RFC for cell entry can, only in the presence of AICAr (Z), increase the uptake of 5-formyltetrahydrofolate, a member of the folate vitamin family that is transported by the RFC, but that does not itself inhibit DHFR.

The current use of antifolates alone or with other cytotoxics has limited tumor range and narrow selectivity. Inclusion of Z potentiation should increase the therapeutic index and may increase the tumor range.

The data presented herein indicates that the uptake of antifolates which act via a mechanism other than inhibition of DHFR (or for those antifolates which primarily act via other mechanisms—at concentrations at which they do not inhibit DHFR) is not enhanced by Z alone. However, if used with a DFHR inhibitor, the uptake of such antifolate is increased. Therefore, in one embodiment, Z or its base and a DHFR inhibitor can be administered with one or more other antifolates that primarily act via mechanisms other than by inhibition of DHFR. Such antifolates include Thymidylate synthase (TMPS) inhibitors, purine synthesis inhibitors and other multi-targeted inhibitors.

TMPS inhibitors include, but are not limited to, 2-amino (or 2-desamino or 2-methyl)-4-oxo-quinazoline, pyrrolopyrimidine, and furopyrimidine antifolates that primarily inhibit TMPS. Tomudex and BW1843U89 are examples of such inhibitors. Also included are variants of such analogs that contain any structural feature (e.g., 7-methyl substitution and/or substitution of an amino acid analog for the glutamic acid analog inherent to so-called classical analogs of folic acid) that abrogates synthesis of poly(gamma-glutamyl) metabolites, such as vamidex.

Purine synthesis inhibitors include, but are not limited to, 5,10-dideazatetrahydrofolates and structurally related compounds such as AG2037 and AG2034 that inhibit one or both of the folate-dependent enzymes of de novo purine synthesis. Also included are variants of such analogs that contain any structural feature (e.g., 7-methyl substitution and/or substitution of an amino acid analog for the glutamic acid analog inherent to so-called classical analogs of folic acid) that abrogates synthesis of poly(gamma-glutamyl) metabolites.

Multi-targeted inhibitors inhibit more than one folate-dependent enzyme or pathway. This class includes, but is not limited to, pemetrexed. Also included are variants of such analogs that contain any structural feature (e.g., 7-methyl substitution and/or substitution of an amino acid analog for the glutamic acid analog inherent to so-called classical analogs of folic acid) that abrogates synthesis of poly(gammaglutamyl) metabolites.

Further, inhibitors of other folate-dependent enzymes that use the RFC as their primary mode of transport may also have their transport potentiated by Z as described above.

The current use of antifolates alone or with other cytotoxics has limited tumor range and narrow selectivity. Inclusion of Z potentiation should increase the therapeutic index and may increase tumor range. For example, if a specific tumor type is resistant to an antifolate because it naturally transports insufficient antifolate to lead to cell kill or insufficient synthesis of required polyglutamates derivatives, inclusion of Z may increase transport sufficiently to overcome this resistance.

The present invention can be used for enhancing the efficacy of antifolates for any use. For example, antifolates are used to treat rheumatoid arthritis (and other autoimmune diseases), psoriasis, and some other pathological states, in addition to cancer. Therefore, Z can be useful in treating any disease in which an antifolate is useful.

Figure 8:
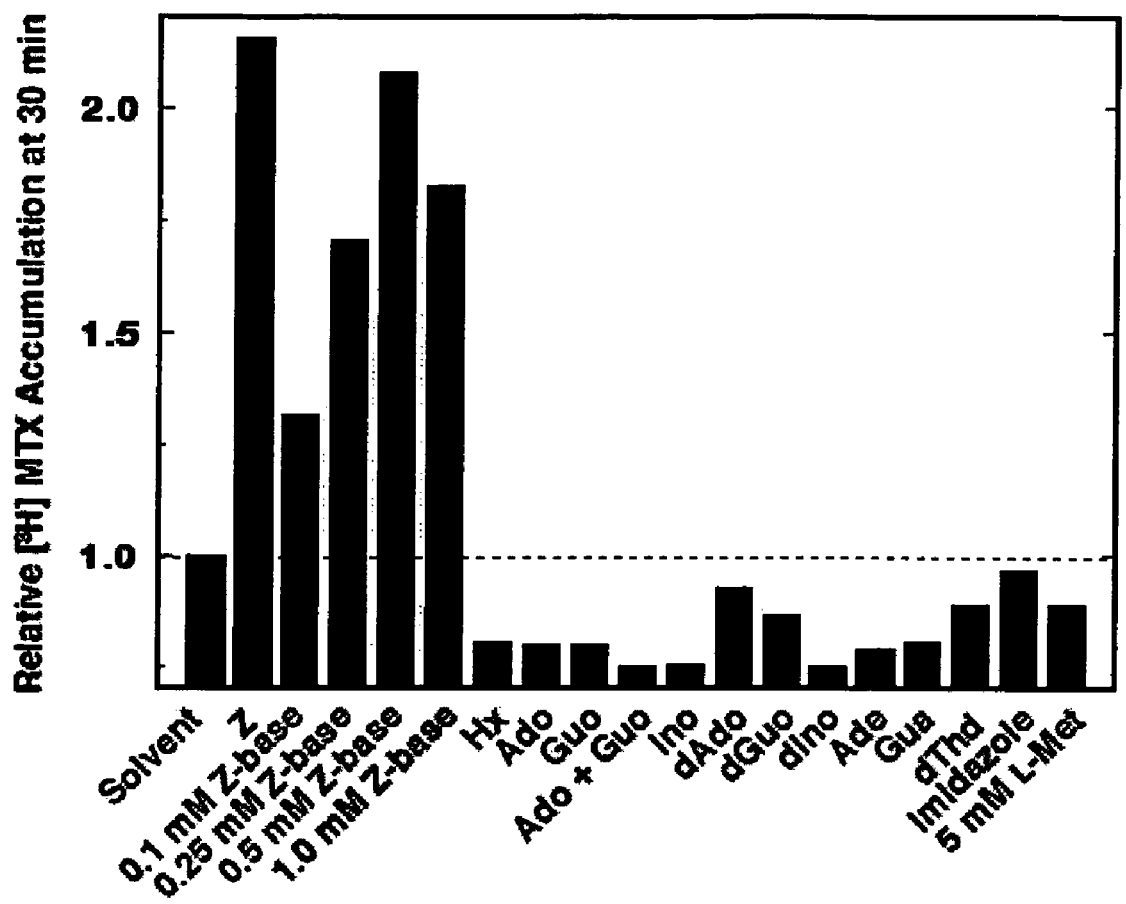
FIG. 8. Comparison of the effects of Z and related compounds on [$^3$H]MTX uptake. Data is shown for the indicated compounds. The concentrations of the various compounds were: methionine (5 mM); Z, adenosine, deoxyadenosine, guanosine, deoxyguanosine, adenosine+guanosine, inosine, deoxyinosine, adenine, guanine, hypoxanthine, thymidine and imidazole (all at 0.5 mM).

The potentiation effect of Z was found to be specific. Other compounds utilized in folate-mediated one-carbon metabolism (formate, methionine, glutamine) or structurally related to Z (e.g., inosine, adenosine, guanosine, etc.; FIG. 8) or synthetic analogs such as pyrazofurin were unable to potentiate [$^3$H]MTX uptake. Potent inhibitors of facilitated uptake of nucleosides such as nitrobenzylthioinosine (1 µM), dipyridamole (10 µM), and dilazep (10 µM) dramatically inhibit potentiation of [3H]MTX uptake by Z in CCRF-CEM cells. This result indicates that Z itself must be transported to potentiate and Z transport can occur via the ENT-1 facilitated diffusion nucleoside transporter, although other transporters may be involved as well in other cell types.

To our knowledge, there are currently no known compounds that potentiate the uptake and metabolism of antifolates via increased activity of the RFC. Likewise there are no compounds that increase synthesis of antifolate polyglutamates. A few metabolic poisons can increase MTX accumulation, but this is mediated by decreased efflux. Our studies indicate that Z does not decrease MTX efflux.

The invention is further described through the following Example which is intended to be illustrative and should not be construed as restrictive.

EXAMPLE 1

Materials and Methods

Materials. Solutions of drugs, nucleosides, and nucleobases for all experiments were standardized using extinction coefficients available in the literature. [$^3$H]MTX (15-33.5 Ci/mmol), and [$^3$H]AMT (53 Ci/mmol) [$^3$H]leucovorin (10-40 Ci/mmol) from Moravek Biochemicals (Brea, Calif.) were typically ≧96% pure when received as analyzed by reversed-phase HPLC with internal standards for p-aminobenzoyl-L-glutamic acid, p-methylaminobenzoyl-L-glutamic acid (isolated from Zn/HCl-treated MTX), AMT, and MTX (and leucovorin, when analyzed). Radiolabeled compounds were re-purified as required. Cell culture. The human T-lymphoblastic leukemia cell line CCRF-CEM [10] and its MTX-resistant subline R2 were routinely cultured as described previously [11]. R2 is MTX-resistant as a result of decreased MTX influx with normal levels of parental DHFR present [12]. Cell lines were verified to be negative for Mycoplasma contamination (Mycoplasma Plus PCR primers, Stratagene, La Jolla, Calif.). For large scale cultures (200-1000 ml), cells were expanded in T-75 flasks containing 60 ml of culture medium and incubated on their sides at 37° and 5% $CO_2$. While cells were still logarithmically growing (3-5×$10^5$ cells/ml), they were used to inoculate spinner flasks at ≧7×$10^4$ cells/ml. The head-space of each spinner flask was sparged for 1-2 min with 5% $CO_2$ through a sterile plugged pipette. The flasks were then sealed and incubated at 37° with stirring at 60 rpm.

MTX polyglutamate synthesis. Synthesis of MTX poly(γ-glutamate) metabolites was measured as previously described [11, 13]. Briefly, CCRF-CEM cells were exposed to [3H]MTX at the indicated concentration and time. At the end of the exposure cells were rapidly chilled to 4 degrees C., harvested by centrifugation at 1000×g for 5 min, washed twice with iced 0.9% NaCl by centrifugation in the same manner. One mL of boiling 50 mM Na-phosphate, pH 5.5 was added, the pellet was triturated and the sample boiled for 5 min. The sample was rapidly cooled to 4 degrees C. Debris was removed by centrifugation as above. The supernatant was further clarified by centrifugation through an Amicon MPS-1 filter unit. The clarified supernatant was adjusted to initial HPLC conditions (0.1 M Na-acetate, pH 5.5 containing 4% (v/v) acetonitrile) by addition of concentrates and commercially available MTX polyglutamate standards were added. A suitable volume was injected onto a reversed-phase HPLC column (C18) and eluted with a gradient of from 4-14% acetonitrile over about 43 min. One min fractions were collected and, after addition of 10 ml scintillation fluid, were quantitated by liquid scintillation counting. Structural assignments were based on alignment of radioactivity with the absorption peaks from the authentic MTX polyglutamate standards. Individual MTX polyglutamates were quantitated based on the specific radioactivity of the [3H]MTX used and the cell number.

Quantitation of folate and antifolate uptake. The method is essentially as follows. Briefly, logarithmically growing (3-5×$10^5$/ml) CCRF-CEM cells were harvested at room temperature by centrifugation at 1000×g for 5 min. After washing with the appropriate medium, cells were suspended at ≈2×$10^7$ cells/ml for use in transport studies. In most cases, the transport medium at 37° was RPMI 1640 containing 10% horse serum and 25 mM HEPES-NaOH, pH 7.5 (pH measured at ambient temperature). This medium was used, rather than an anion-deficient buffer or a buffered balanced salt solution, for consistency because the original observation of potentiation was made in this medium and because the same medium can be used for MTX metabolism studies (below). However, potentiation of uptake by AICAr is also observed in both anion-deficient (MHS) and buffered balanced salt solutions (see Results). Anion-free MHS contains 250 mM sucrose and 20 mM HEPES, titrated to pH 7.4 with MgO. HBSS [5] contained 107 mM NaCl, 26.2 mM $NaHCO_3$, 5.3 mM KCl, 1.9 mM $CaCl_2$, 1 mM $MgCl_2$, 7 mM glucose, and 20 mM HEPES; the mixture was titrated to pH 7.4 with NaOH [5]. Cells were pre-incubated with compounds of interest and uptake was initiated by addition of [$^3$H]MTX (typically 2 µM) or [$^3$H]leucovorin (1 µM). Uptake was measured as a function of time for 30 min (for rate and extent measurements) or over 5 min (studies requiring initial velocities). Uptake was linear with respect to time over at least 5 min. Uptake was terminated by diluting 100 µL samples into 1 ml of iced 0.9% NaCl. Cells were recovered by centrifugation for 10 sec at 12,500×g in the horizontal rotor of a Beckman Microfuge E; this procedure was verified to pellet >99.7% of the cells. The supernatant was aspirated. The cell pellet was washed once with 1 ml iced 0.9% NaCl and centrifuged as above. The washed pellet was solubilized in 1 ml of 0.3% Triton X-100 by incubation for 60 min at 37° C. The solubilized pellet was transferred to a scintillation vial, 10 ml of Liquiscint (National Diagnostics, Atlanta, Ga.) was added and radioactivity was quantitated in a Beckman Model LS6500 liquid scintillation counter. Separate samples at the longest incubation time used in a particular experiment were harvested for HPLC analysis of intracellular contents as above, except that after the second wash the pellets were extracted with 1 ml boiling 0.1 M Na-phosphate, pH 5.5. The extract was clarified by centrifugation and the supernatant was filtered through an MPS-1 filter unit (Amicon) prior to HPLC analysis. In typical samples, >90% of the intracellular radiolabel eluted with MTX, MTX-γ-Glu, and (rarely) MTX-γ-$(Glu)_2$.

Inhibition of MTX uptake. Inhibition of uptake was measured as described above in cells that were pre-incubated for 10 min with 1 µM TMTX±500 µM Z. Graded concentrations of competitor were mixed with [$^3$H]MTX and added together at time zero. Duplicate samples were removed at 5 min and processed as described above. Uptake of radiolabel was verified to be linear over 5 min and thus represents the initial velocity. $IC_{50}$ values for [$^3$H]MTX uptake were determined graphically from plots of uptake relative to solvent-treated control versus competitor concentration.

Figure 4:
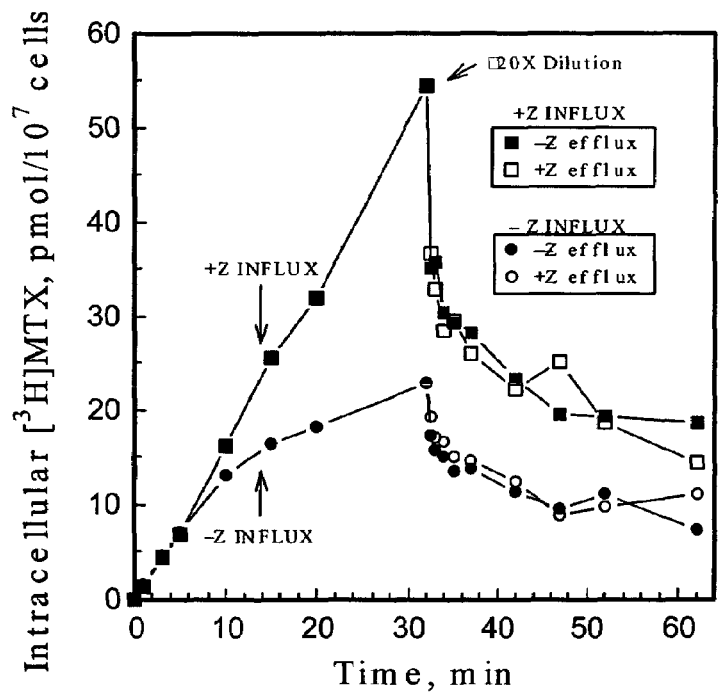
FIG. 4. Efflux of [$^3$H]MTX in the absence or presence of Z after loading in the absence or presence of Z. CCRF-CEM cells at $2.1\times10^7$ cells/ml were incubated for 5 min±500 μM Z before addition of [$^3$H]MTX to a final concentration of 2 μM (3 μCi/ml). Uptake in the absence (closed circle) or presence (closed square) of Z was quantitated as described in Methods. Aliquots of cells ±Z were washed starting at 20 min and efflux ±Z for each uptake condition was initiated at 32 min as described in Methods: −Z→−Z (closed circle); −→+Z (open circle); +Z→−Z (closed square); +Z→+Z (open square). Just previous to the start of efflux, the last uptake samples were taken.

Quantitation of MTX efflux. [$^3$H]MTX efflux from CCRF-CEM cells was measured as follows. Three ml CCRF-CEM cells at $2.2\times10^7$ cells/ml were incubated at 37° for 5 min±500 µM Z before addition of [$^3$H]MTX to a final concentration of 2 µM (3 µCi/ml). Samples (100 µL) were taken at the time indicated (FIG. 4) and processed (above) to monitor uptake. After 20 min uptake, 2×1 ml were removed to separate tubes from both the ±Z uptake samples. These 4 samples were centrifuged at ambient temperature for 5 min at 1000×g. After aspiration of the supernatant, the cell pellets were again placed at 37° and 2 ml warmed transport medium ±Z, respectively, was added to each pair. Samples of 200 µL were taken at the indicated times and processed. The warmed medium was added at 30 sec intervals starting at 32 min and a zero sample was taken as soon as the medium was added and the cells were evenly suspended. The last uptake samples were taken at 32 min, just before initiation of efflux.

Quantitation of protein-bound [$^3$H]MTX. The level of protein-bound MTX (presumably DHFR) was determined as previously described [14]. CCRF-CEM cells were exposed to [3H]MTX at the indicated concentration and time, and then harvested and washed as described above. The cell pellet was frozen immediately at less than or equal to −80 degrees C. To process, 1 ml iced lysis buffer was added to the pellet immediately after removal from the freezer and the pellet was dispersed with a pasteur pipette. Freshly made lysis buffer contained (final concentrations): 50 mM citric-citrate, pH 6.0, 50 mM 2-mercaptoethanol, 50 µM NADPH (in 25 mM Tris, pH7.5), and 2 mg/ml bovine serum albumin. The sample was freeze-thawed once in dry ice-methanol, centrifuged at 1860×g for 10 min to remove debris and then further clarified by centrifugation through an Amicon MPS-1 filter unit. A 5 ml centrifugal column was prepared at 4 degrees C. in a 5 ml plastic syringe plugged with a porous plastic frit overlaid with a GF/C glass fiber filter cut with a #8 cork borer, then packed with Sephadex G-25 (Medium) in 50 mM citric-citrate, pH 6.0 to the 5 ml line, and centrifuged 5 min at 1000×g (0°) to expel liquid. The clarified supernatant (0.5 ml) was applied to the top of the column, the column was re-centrifuged at 1000×g (5 min) and the pass-through was collected in a 7 ml scintillation vial. After addition of scintillation fluid (5.5 ml), the sample was quantitated by liquid scintillation counting. Protein-bound [3H]MTX was quantitated based on the specific radioactivity of the [3H]MTX used and the cell number.

Subcellular fractionation. CCRF-CEM cells ($2.6\times10^7$/ml; 5 ml) were preincubated with 2 µM TMTX or 2 µM TMTX+ 500 µM Z for 10 min and then [$^3$H]MTX (2 µM; 0.2 µCi/ml) was added and uptake was allowed to proceed for 30 min. Cells were diluted 9-fold in iced 0.9% NaCl, centrifuged at 1000×g for 5 min and washed once with 40 ml iced saline. All subsequent steps were performed at 4°. Cells were homogenized as previously described [8], except that hypotonic buffer at 20-fold the packed cell volume was used, and the homogenate was centrifuged for 6 min at 1000×g to yield a nuclear pellet (also containing unlysed cells and large debris) and a post-nuclear supernatant (PNS). Based on controls using nonradiolabeled cells, >91% of the cells would be lysed during homogenization. The PNS was centrifuged at 17,000×g to yield a combined mitochondria-lysosome pellet. The resulting supernatant was centrifuged at 100,000×g for 60 min to yield the 100,000×g supernatant (cytosol). The 100,000×g pellet (microsomes) and the combined mitochondria-lysosome pellet were each washed in isotonic buffer [8] and centrifuged at their respective g-forces. All pellets were solubilized in 0.3% Triton X-100 by incubating at 37° for 1 hr; 1 ml was transferred to a scintillation vial for quantitation. Triton X-100 was added to the cytosol to a final concentration of 0.3% and a 1 ml aliquot was quantitated. Radioactivity in each fraction was corrected for a blank containing 0.3% Triton X-100. Relative radioactivity is the percent of the pmol [$^3$H]MTX recovered in a fraction relative to the total pmol [$^3$H]MTX recovered in all four fractions (+TMTX, 338.4; +TMTX+Z, 641).

Inhibition of growth of human cell lines in vitro. Inhibition of growth of CCRF-CEM in continuous and intermittent drug exposures was measured. $EC_{50}$ values were determined from plots of percent control growth versus the logarithm of drug concentration.

HPLC analysis. Analytical HPLC was performed on a Rainin Instruments HPLC system using the Dynamax controller and data capture module run on a Macintosh computer. Eluate was monitored at 280 and 254 nm. RP-HPLC was performed on a C18 column (0.4×25 cm; Rainin Microsorb, 5µ) at 25°.

Results

Effect of Z on MTX polyglutamate synthesis by CCRF-CEM cells. In CCRF-CEM cells, the simultaneous presence of 500 µM Z is able to increase both total drug (3-fold) and MTX polyglutamates (n≧2) accumulation (3.5-fold) after 4 hr exposure to 2 µM [$^3$H]MTX (Table 1).

TABLE 1

Synthesis of methotrexate polyglutamates ($4-NH_2-10-CH_3-PteGlu_n$) by CCRF-CEM human leukemia cells in the presence and absence of 500 µM Z

| Conditions | Total drug (pmol/10$^7$ cells) | $4-NH_2-10-CH_3-PteGlu_n$ (MIX polyglutamates) (pmol/10$^7$ cells) | | | | | | |
|---|---|---|---|---|---|---|---|---|
| | | n = 1(MTX) | 2 | 3 | 4 | 5 | n ≧ 2 | N ≧ 3 |
| MIX | 53.8 | 26.2 | 23.8 | 2.3 | 1.4 | 0.1 | 27.6 | 3.8 |
| MTX + Z | 165.7 | 70.1 | 73.0 | 16.6 | 5.4 | 0.6 | 95.6 | 22.6 |

Of particular interest is the finding that the longer, better-retained MTX polyglutamates (n≧3) are increased 6-fold by the presence of Z. If, after 4 hr uptake, cells are washed free of [$^3$H]MTX (and Z) and allowed to efflux for 2 hr, cells initially treated with Z retain much higher levels of drug (data not shown). Increased MTXGn accumulation is also observed at 1 and 10 µM [$^3$H]MTX in the presence of 500 µM Z (data not shown). Thus, Z potentiates the accumulation of cytotoxic MTXGn metabolites in human leukemia cells.

Effect of Z concentration on MTX influx potentiation. Since an effect of Z on influx is one likely explanation for the potentiation seen above, the effect of Z on uptake of 2 µM

Figure 2:
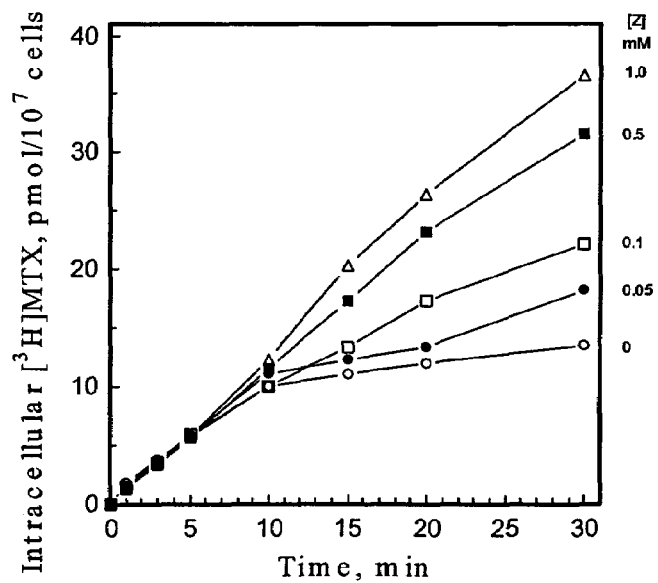
FIG. 2. Concentration-dependence of Z potentiation of [$^3$H]MTX uptake in CCRF-CEM cells. CCRF-CEM cells at $2\times10^7$ cells/ml were pre-incubated for 5 min with various concentrations of Z before addition of [$^3$H]MTX to a final concentration of 2 μM (3 μCi/ml). Aliquots (100 μL) were removed at the indicated times and processed as described in Methods. Z concentrations are: zero (water; open circle); 0.05 mM (closed circle); 0.1 mM (open square); 0.5 mM (closed square); and 1.0 mM (open triangle). This experiment was repeated with similar results.

[³H]MTX by CCRF-CEM cells was assayed. Z was added 5 min before [³H]MTX addition and influx was assayed over 0-30 min to quantitate both initial influx velocity ($v_i$; 0-5 min) and extent (30 min) levels (FIG. 2). Z does not affect $v_i$ under these conditions. After 5-10 min of linear uptake, the influx rate in the absence of Z falls dramatically and accumulation approaches a plateau level; the slight continued increase is a result of MTX polyglutamate synthesis initiating and ongoing synthesis of DHFR which binds MTX tightly. In contrast, in the presence of 0.05-1.0 mM Z, uptake continues after 10 min at a rate that is dependent on the concentration of Z; at the highest Z levels there is little indication of a plateau at 30 min. Z at 0.5-1.0 mM increases MTX accumulation at 30 min by $\geq$3-fold. HPLC analysis showed that at 30 min 86% of intracellular radiolabel is MTX and 12% is MTX-γ-Glu in the absence of Z, while 83% is MTX and 7.5% is MTX-γ-Glu with <1% MTX-γ-(Glu)$_2$ in the presence of Z. Thus, neither degradation of [³H]MTX to rapidly transported moieties nor increased MTXGn synthesis accounts for the potentiation of uptake induced by Z. The 3-fold increased level of MTX at 30 min in the presence of Z suggests that the increased MTXGn accumulation of Table 1 is primarily a result of increased availability of substrate (MTX) for polyglutamylation. Additional data (not shown) indicate that 0.5 mM Z potentiates [³H]MTX influx in the K562 human chronic myelogenous leukemia cell line with a similar lag and increase in accumulation at 30 min; thus potentiation by Z is not restricted to CCRF-CEM cells or one cell lineage.

Figure 3A:
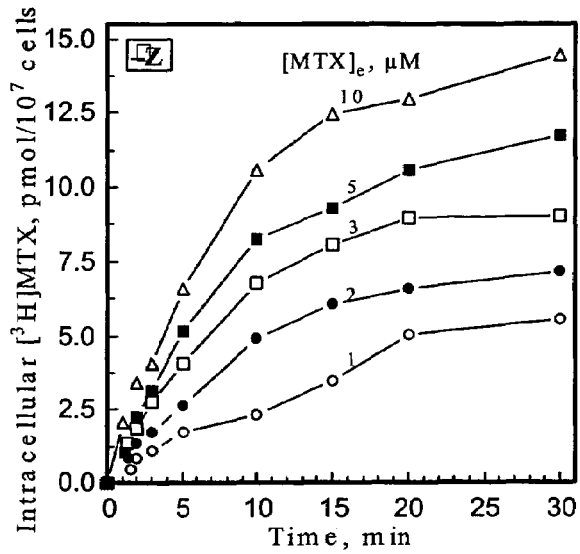
FIGS. 3A and 3B. Dependence of [$^3$H]MTX uptake in CCRF-CEM cells on methotrexate concentration in the presence and absence of Z. Cells were pre-incubated with 500 μM Z for 5 min and then [$^3$H]MTX was added at the indicated concentration (3 μCi/ml). Aliquots (100 μL) were removed at the indicated times and processed as described in Methods. The entire experiment was repeated with similar results.
Figure 3B:
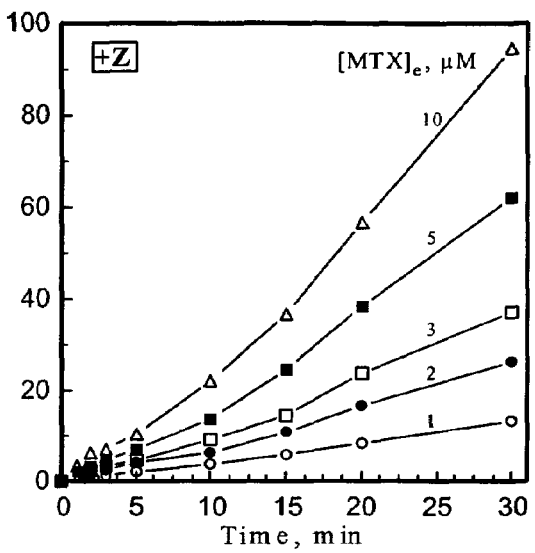

Effect of MTX concentration of uptake potentiation by Z. Influx was studied as a function of [³H]MTX concentration ±0.5 mM Z (FIG. 3). $V_i$ values (0-5 min) are the same ±Z (note change in scale), but Z potentiates 30 min accumulation at all MTX concentrations (1-10 μM) and potentiation is highest (6-fold) at 10 μM (note change in scale). The ≈10 min delay before the onset of Z potentiation is seen at all levels of MTX. Analysis of the $v_i$ (0-5 min) data show that in the absence of Z, the $V_{max}/K_t$=0.44, while in the presence of Z, the $V_{max}/K_t$=0.47, suggesting that the kinetics at the earliest times are unaffected by Z.

Effect of preincubation time with Z on the onset and/or extent of potentiation. In the above studies, Z was preincubated with CCRF-CEM cells for 5 min before [³H]MTX addition; 5 min was chosen because most nucleosides are rapidly transported and metabolized. Since there is an apparent delay of ≈10 min before onset of potentiation by Z (FIG. 2), the effect of preincubation time with 0.5 mM Z on the time of onset and extent of potentiation was tested. Whether preincubation of cells with Z was for 5-20 min or even if Z was added simultaneously with [³H]MTX, the time course was identical to that of FIG. 2 (i.e., potentiation did not occur until ≈10 min after [³H]MTX addition). Even if Z was added 10 min after [³H]MTX (data not shown), there was still a delay of $\geq$5 min before potentiation of [³H]MTX uptake was observed and full potentiation occurred only after 5-10 min more (data not shown).

Effect of Z on MTX efflux. Increased MTX accumulation over 30 min could result from continued influx and/or decreased efflux. [³H]MTX efflux from CCRF-CEM cells was measured after uptake in the presence or absence of 0.5 mM Z. Efflux in each sample was then measured in the presence or absence of 0.5 mM Z (cross-over design). No significant difference was noted in the efflux rates (FIG. 4; $t_{1/2}$ ranged from 14.6-18.7 min), which suggests that Z affects influx only.

Effect of Z on protein-bound intracellular MTX Levels of protein-bound MTX [14] (presumably dihydrofolate reductase; DHFR) are essentially identical in the absence or presence of 0.5 mM Z over the entire 30 min time course of uptake (data not shown); at 30 min, protein-bound levels are 6.4±0.1 pmol/10⁷ cells and 5.4±0.4 pmol/10⁷ cells in the absence and presence of 0.5 mM Z, respectively. Thus, the increased influx rate in the presence of Z is not a result of induction of a high-affinity binding protein that sequesters MTX. These data again support an effect of Z on influx.

Figure 5:
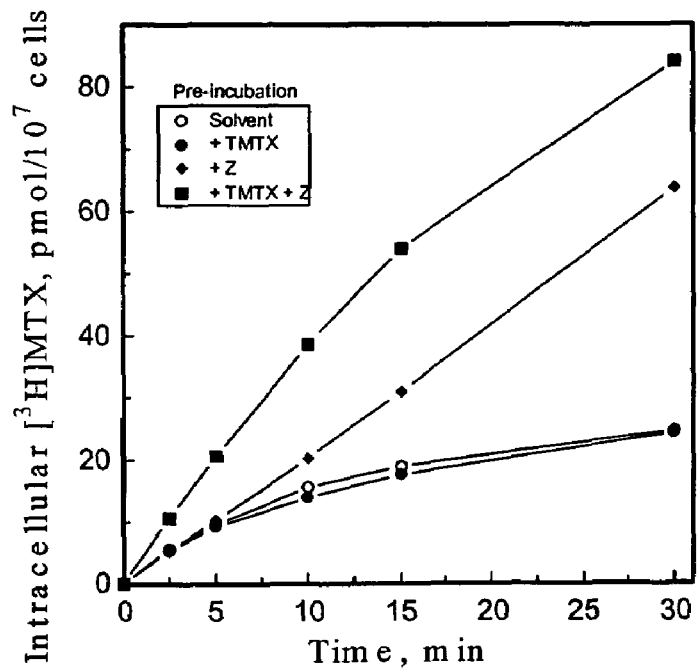
FIG. 5. Effect of the lipophilic dihydrofolate reductase inhibitor trimetrexate (TMTX) on potentiation of [$^3$H]MTX uptake by 0.5 mM Z. CCRF-CEM cells were pre-incubated for 10 min with solvent alone (open circle), 1 μM TMTX (closed circle), 0.5 mM Z (closed diamond), or TMTX+Z (closed square). At 10 min, [$^3$H]MTX (2 μM and 0.75 μCi/ml final) was added and uptake was quantitated as described in Methods.

Effect of DHFR inhibition on potentiation by Z. Studies were undertaken to determine whether MTX itself, inhibition of DHFR, or other inhibition of folate metabolism is sufficient to initiate and sustain the potentiating effect of Z. Trimetrexate (TMTX) is a potent, lipophilic DHFR inhibitor that rapidly enters cells and does not utilize the RFC [7]. The $v_i$ for [³H]MTX uptake is the same for CCRF-CEM cells preincubated for 10 min (the time of the delay in potentiation) ±2 μM TMTX (FIG. 5); the extent of [³H]MTX accumulation at 30 min in the presence of TMTX is 90-100% that in the absence of TMTX. If Z is present with TMTX in the preincubation, there is no delay in potentiation of [³H]MTX uptake and the $v_i$ is immediately increased (FIG. 5). This result indicates that MTX per se or its metabolites are not required to initiate potentiation, but suggest that inhibition of folate metabolism is required and that DHFR inhibition is sufficient to initiate and sustain potentiation by Z.

Figure 6:
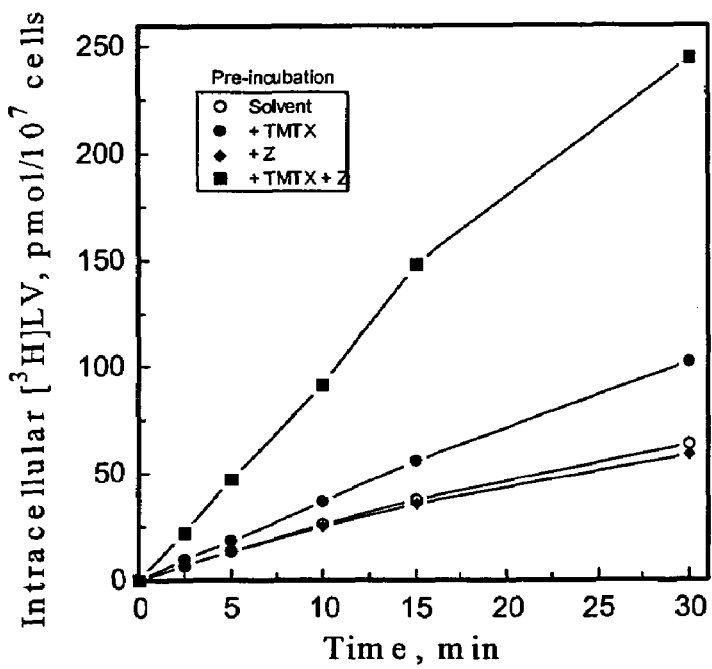
FIG. 6. Effect of the lipophilic dihydrofolate reductase inhibitor trimetrexate (TMTX) on potentiation of [$^3$H]leucovorin (LV) uptake by 0.5 mM Z. CCRF-CEM cells were pre-incubated for 10 min with solvent alone (open circle), 1 μM TMTX (closed circle), 0.5 mM Z (closed diamond), or TMTX+Z (closed square). At 10 min, [$^3$H]LV (1 μM and 0.25 μCi/ml) was added and uptake was quantitated as described in Methods.

These findings were reinforced by uptake studies with the reduced folate leucovorin (LV; 5-formyltetrahydrofolate). Pre-incubation of CCRF-CEM cells with Z alone does not potentiate uptake of 1 μM [³H]LV (FIG. 6) consistent with a requirement for inhibition of folate metabolism in initiating potentiation. Preincubation of CCRF-CEM with TMTX alone causes a small increase in $v_i$ (1.4-fold) and 30 min accumulation (1.6-fold) of 1 μM [³H]LV (FIG. 6). If cells are preincubated with Z+TMTX, however, there is no lag before potentiation of [³H]LV uptake is observed, and the initial rate (3.6-fold) and extent (3.8-fold) of [³H]LV uptake are both substantially increased (FIG. 6). These data are again consistent with DHFR inhibition being sufficient to initiate potentiation by Z and show that reduced folates are also subject to potentiation and MTX itself need not be involved. The absence of potentiation by Z alone again shows that increased uptake is not a result of simple increased heteroexchange of an organic anion at high intracellular concentration (i.e., ZMP).

Effect of removal of Z after initiation of potentiation. As noted above, potentiation of [³H]MTX uptake by Z requires about 10 min to initiate in the absence of TMTX and then continues through at least 30 min. When potentiation was initiated by preincubation with Z+TMTX, and both were then removed by washing, the potentiating effect on [³H]MTX uptake was lost after about 60 min (data not shown). The potentiating effect is thus sustained for a significant period once it is initiated.

Subcellular location of [³H]MTX accumulated during Z potentiation. Using a previously published procedure [8] to separate CCRF-CEM cytosol from a combined mitochondrial/lysosomal fraction, the subcellular distribution of [³H]MTX at 30 min of the time course ±Z was determined (Table 2). There was no qualitative difference between the distribution ±Z. No significant radioactivity was recovered in the mitochondrial/lysosomal fraction or in the microsomal fraction. More than 91% of the total recovered radioactivity was in the cytosolic fraction. If the nuclear pellet, which could contain unbroken cells and residual cytosol, is excluded and only the post-nuclear supernatant is considered, >98% of the radioactivity is cytosolic (100,000×g supernatant). HPLC analysis of the material in the cytosol showed that it was >90% MTX or metabolites.

TABLE 2

Subcellular localization of [³H]MTX (2 μM, 0.2 μCi/ml)
after 30 min uptake in CCRF-CEM cells pre-incubated with
2 μM TMTX or 2 μM TMTX + 500 μM Z

| | Subcellular Fraction | | | |
|---|---|---|---|---|
| | +TMTX | | +TMTX + Z | |
| | [³H]MTX/ fraction (pmol) | Relative radio-activity (%) | [³H]MTX/ fraction (pmol) | Relative radio-activity (%) |
| Nuclear Pellet | 35.5 | 10.5 | 29.5 | 4.6 |
| Mito-Lysosomes | 1.3 | 0.4 | 2.5 | 0.4 |
| Microsomes | 0.7 | 0.2 | 1.1 | 0.2 |
| Cytosol | 300.3 | 88.9 | 606.1 | 94.8 |

Effect of Z on kinetic parameters of MTX influx. MTX influx is typically mediated either by the reduced folate carrier (RFC) or a membrane-bound folate-binding protein (FBP). The μM MTX concentration-dependence during potentiation (FIG. 3) and the minute-scale time-dependence (FIGS. 2 and 3) are both consistent with the RFC being involved and inconsistent with FBP. Since preincubation with Z in the presence of TMTX eliminates the lag before potentiation is evident (FIG. 5), it is thus possible to determine the Michaelis kinetic constants for transport during potentiation. The data (Table 3) show that TMTX causes a small apparent increase in the $K_m$ for MTX, however Z addition does not further affect the $K_m$, but does increase the $V_{max}$ by ≈3-fold. The $K_m$ values are consistent with RFC mediating this effect and since only $V_{max}$ is affected it indicates that more transporter has become active (see below) or that individual transporter molecules are operating at an increased rate. Assuming a value of 0.55 pL/CCRF-CEM cell [15], influx at 30 min only reached equilibration at 1 μM; in the presence of 0.5 mM Z, transport was concentrative ($[MTX]_i/[MTX]_e \geq 1.9$) at all MTX concentrations from 1-10 μM.

TABLE 3

Kinetic constants for influx of [³H]MTX by
CCRF-CEM cells in the presence and absence of Z

| Pre-incubation Conditions | $K_t$ (μM) | $V_{max}$ (pmol/min/10⁷ cells) | $V_{max}/K_t$ |
|---|---|---|---|
| Solvent | 3.0 ± 0.8 | 5.8 ± 0.9 | 1.95 |
| +TMTX | 5.3 ± 0.6 | 7.2 ± 0.6 | 1.36 |
| +TMTX + Z | 5.1 ± 0.1 | 19.8 ± 2 | 3.9 |

Further evidence supporting the RFC as mediating the Z-induced potentiation of MTX uptake. If the RFC mediates the enhanced [³H]MTX uptake in the presence of Z, the potentiated uptake should have other characteristics in common with that of the RFC. The effect of temperature (37° vs. 27°) on the $v_i$ and extent at 30 min of [³H]MTX uptake in the absence and presence of preincubation with 0.5 mM Z (both pre-incubations in the presence of 1 μM TMTX) was assessed. The data show that in the absence of Z, the $Q_{10}$ for $v_i$ of uptake is 4.6±0.3 (n=2), while in the presence of Z the $Q_{10}$ is 5.9±0.1 (n=2). The temperature-dependence of $v_i$ indicates that influx ±Z is facilitated ($Q_{10} > 3$) and the values ±Z are similar; the slightly lower value –Z may reflect the much lower influx rates observed, especially at 27°. If the extent of uptake at 30 min is compared, the $Q_{10}$ values are again similar (3.45±0.15 and 3.65±0.15 in the absence and presence of Z, respectively). These data are consistent with the RFC mediating potentiation by Z.

Effect of competitors of the RFC on the Z-induced potentiation of [³H]MTX uptake. If the RFC mediates the increased [³H]MTX influx in the presence of Z, the uptake should be inhibited in a quantitatively similar manner by alternate substrates of the RFC and by known RFC inhibitors. Inhibition of the $v_i$ of uptake was measured after pre-incubation of CCRF-CEM cells either with TMTX alone (measuring inhibition at the RFC) or with TMTX+Z (measuring inhibition during Z potentiation). Inhibition studies were carried out as described in Methods after a 10 min pre-incubation with 1 μM TMTX alone (inhibition of the RFC) or 1 μM TMTX=0.5 mM Z (inhibition of Z potentiated influx). All studies were carried out in standard transport medium. Inhibitory potency was measured in two series of experiments and AMT was included in each series as an internal control. Values are average±range of two determinations. The results are shown in Table 4. The results indicate that folate analogs recognized as efficient substrates by the RFC (i.e., aminopterin, (6R,S)-LV, ZD 1694, BW1843U89, and DDATHF) had similar potencies as inhibitors of [³H]MTX influx in both the absence and presence of Z and the potencies are similar to the published $K_t$ values of these folate analogs for the RFC [2,5,7]. In contrast, folic acid, which is a poor substrate for the RFC was a poor competitor of [³H]MTX influx in both the absence and presence of Z. Folic acid, unlike the folate analogs, showed a plateau in inhibition at 60-70% (data not shown); this plateau was observed ±Z. For comparison, the inhibitory potency of AMT, (6R,S)-LV, and folic acid were also measured in the absence of both TMTX and Z (data not shown) and the values were comparable to those in the presence of TMTX alone (Table 3). For table 3, standard uptake conditions were used except that cells were pre-incubated in the presence of solvent (water), 1 μM TMTX, or 1 μM TMTX+0.5 mM Z. TMTX was used to initiate potentiation by Z prior to addition of MTX. Values are average±range for duplicate determinations. The potency and pattern of competition are consistent with the RFC mediating the uptake potentiated by Z.

TABLE 4

Inhibition of initial velocity of [³H]MTX
influx by antifolates and folic acid.

| | IC50, μM Inhibitor | |
|---|---|---|
| Competitor | +TMTX | +TMTX + Z |
| MIX | 11.1 ± 0.2 | 10.7 ± 0.8 |
| AMT | 3.7 ± 0.2 | 2.6 ± 0.3 |
| (6R,S)-LV | 2.6 ± 0.1 | 2.7 ± 0 |
| PteGlu | 18.6 ± 0.6 | 18.5 ± 1.1 |
| AMT | 4.0 ± 0.6 | 4.4 ± 0.4 |
| ZD1694 | 2.4 ± 0.5 | 3.4 ± 0.5 |
| BW1843U89 | 1.0 ± 0.1 | 1.3 ± 0.4 |
| DDATHF | 1.0 ± 0.2 | 1.2 ± 0.4 |

Effect of Z on [³H]MTX transport in an RFC-defective CCRF-CEM subline (R2) and its RFC-transfectant clones. Determining whether [³H]MTX uptake is potentiated by Z in a CCRF-CEM subline that is deficient in the RFC (R2) is another approach to defining the transport system involved. Under standard conditions (e.g., FIG. 2), there was essentially no uptake by R2 of [³H]MTX in the presence or absence of 500 μM Z, while Z potentiated uptake in parental CCRF-CEM cells (data not shown). TMTX was present in both conditions to establish DHFR inhibition, since that appears to be required. Since CCRF-CEM and R2 should be isogenic except for the RFC alteration of R2, the lack of potentiation by Z in R2 is consistent with the RFC, and not an undescribed influx system, mediating the uptake that is affected by Z. Consistent with this result is the finding that the potency of MTX against R2 in continuous exposure ($EC_{50}$, 2200 nM) was unaffected by the presence of 50 μM Z ($EC_{50}$, 2200 nM). If Z activated an RFC-independent pathway, it would be expected that increased MTX influx via this pathway would increase the potency against R2. Neither the parent nor R2 grown in folate-replete medium expresses FBP thus this data further supports the suggestion that FBP is not involved.

[$^3$H]MTX uptake potentiated by Z is mediated by the reduced folate carrier (RFC). To further confirm the involvement of RFC, we transfected the RFC-negative R2 subline of CCRF-CEM with a human RFC expression plasmid. Stably expressing clones were selected in 2 nM leucovorin (LV)-containing RPMI 1640 medium (R2 cannot replicate in this medium, while parental RFC-expressing CCRF-CEM can replicate). Multiple independent clones showed [$^3$H]MTX transport extents at 30 min similar to CCRF-CEM. Transport is potentiated by Z to a similar extent in the transfected clones and in CCRF-CEM. This supports RFC as mediating the transport potentiated by Z.

Figure 7:
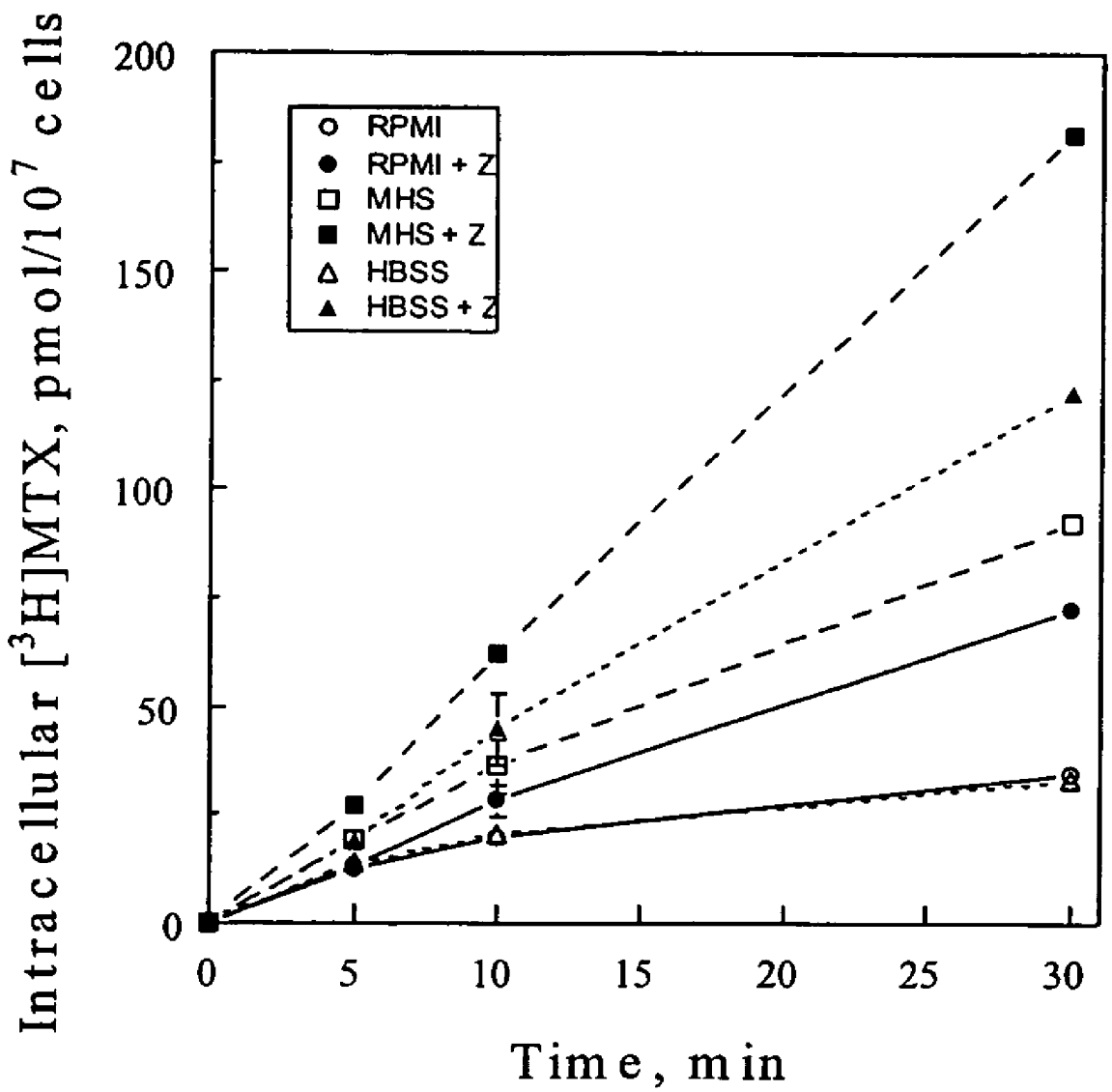
FIG. 7. Effect of transport medium composition on potentiation of [$^3$H]MTX uptake by 0.5 mM Z. CCRF-CEM cells were harvested and washed thoroughly with either standard transport medium (open circle, closed circle; RPMI 1640/10% horse serum/25 mM HEPES-NaOH, pH 7.5) or MHS (open square, closed square; anion-free isotonic buffer) or HBSS (open triangle, closed triangle; HEPES-buffered balanced salts solution). Cells were then pre-incubated for 10 min with either solvent (water; open symbols) or 0.5 mM Z (closed symbols); uptake was initiated by addition of [$^3$H] MTX to 2 μM. Samples were taken at the indicated time points and processed as described in Methods.

Potentiation by Z of [$^3$H]MTX influx in anion-deficient and buffered balanced salts media. The ability of 0.5 mM Z to potentiate uptake of [$^3$H]MTX in MHS and HBSS was compared to the standard medium (RPMI 1640 containing 10% horse serum and 25 mM HEPES-NaOH, pH 7.5 (FIG. 7). Influx in standard medium and HBSS is essentially identical over the 30 min time course; [$^3$H]MTX accumulation at 30 min is similar and shows the same plateau. Influx in anion-free MHS has a ≈4.4-fold faster $v_i$ and a 2.7-fold higher extent of accumulation at 30 min. Z potentiates the influx in all three systems, albeit with different characteristics. The standard medium shows the typical (FIG. 2) 5-10 min lag before initiation of potentiation. HBSS and MHS appear to show no or less lag, and the $v_i$ values are 1.4- to 1.9-fold those observed in the absence of Z. Potentiation of accumulation at 30 min is similar in standard medium and MHS (≈2-fold), but is higher (≈4-fold in HBSS). The appearance of potentiation in all buffers appears to rule out heteroexchange of MTX for an anion (i.e., ZMP) generated after Z transport as a mechanism. Note the data in MHS and HBSS also rule out potentiation by acute sensing of extracellular folate deficiency that Z somehow mimics, since Z potentiation still occurs even though these media do not contain any folate. Consistent with this suggestion is the finding (data not shown) that Z potentiation still occurs to the same extent when folate-replete cells are thoroughly washed in 0.9% NaCl and placed in RPMI medium lacking folic acid (RPMI 1640, 2.2 μM folic acid) immediately before influx is measured.

Initial studies on the mechanism of Z potentiation of [$^3$H]MTX influx. The rapid onset of potentiation induced by Z in CCRF-CEM cells suggests that new protein synthesis may not be required. We previously showed that protein synthesis in CCRF-CEM is completely inhibited by 10 μg/ml cycloheximide (CHX) within 5 min [9]. When CCRF-CEM cells were preincubated with 10 μg/ml CHX for 10 min, and 0.5 mM Z was added for the last 5 min, potentiation still occurred as in FIG. 3. These data show that protein synthesis is not required for potentiation by Z. Because of the sequence in which the incubation was performed, the data rule out a requirement for new protein synthesis both in the MTX transport system and in metabolism of Z. These data suggest that the RFC is activated directly or indirectly.

We have also investigated how specific the potentiation is for Z. The ability of a number of purines, thymidine, and imidazole (all at 0.5 mM), and methionine (5 mM) to potentiate [$^3$H]MTX influx by CCRF-CEM cells at 30 min after a 10 min pre-incubation with TMTX+Z was quantitated (FIG. 8). Adenosine, deoxyadenosine, guanosine, deoxyguanosine, adenosine+guanosine, inosine, deoxyinosine, adenine, guanine, hypoxanthine, and thymidine (all at 0.5 mM) do not potentiate [$^3$H]MTX uptake. The only compound that also potentiates is Z-base, the aglycone of Z. The ribose of Z is thus not essential for causing potentiation. These data also suggest that Z-base is not produced from Z in the serum-containing uptake medium and thus Z is the actual active moiety. Thus potentiation is not a general property of nucleosides or nucleobases and may be limited to Z and closely related compounds. These data further suggest that a simple anion-exchange mechanism does not cause Z potentiation.

Effect of Z co-incubation on the growth inhibitory potency of MTX. Since Z increases MTX uptake and MTX polyglutamate accumulation, Z would be expected to increase the growth inhibitory potency of MTX against CCRF-CEM cells. Inhibitory potency was quantitated ($EC_{50}$) as the concentration effective at inhibiting growth by 50% relative to an untreated culture as described in Methods. Z at 50 μM is non-toxic to CCRF-CEM cells during 120 hr exposure ($EC_{50}$, 130±20 μM; n=2). Z at 100 μM is non-toxic to CCRF-CEM cells during 0-24/120 hr exposure ($EC_{50}$, 410±50 μM; n=2). Values presented are average±S.D. for n>2 and average±range for n=2. The presence of 50 μM Z (nontoxic) does not significantly increase MTX potency during continuous (120 hr) drug exposure (Table 5). However, when "pulse" exposure is used (MTX and 100 μM Z are present only for 0-24 hr of the 120 hr growth period), inhibitory potency increased 2-fold relative to MTX alone. Of significance is the finding that the concentration-response curve of MTX alone in 0-24 hr pulse exposure has a shallower slope than that for continuous exposure, but addition of 100 μM Z restores the steeper slope. Thus, the concentration to inhibit growth by 80% is 3- to 4-fold lower in the presence of Z; $EC_{50}$ data may therefore underestimate the biological potency. This result shows that enhancement of MTX uptake and metabolism by Z is translated into increased cytotoxicity. $EC_{50}$ potency of AMT was also increased ≈2-fold by the presence of Z in 0-24 hr exposure (Table 5). Both results also show that Z, which could potentially serve as a purine source, did not reverse the growth inhibitory effect of MTX or AMT.

TABLE 5

Effect of Z on growth inhibitory potency of MTX and aminopterin in continuous and "pulse" exposure.

| Drug | Drug exposure time (hr/total hr) | [Z] (μM) | $EC_{50}$ (nM) | N |
|---|---|---|---|---|
| MTX | 0-120/120 | 0 | 14.5 ± 0.5 | 2 |
|  |  | 50 | 13.5 ± 0.5 | 2 |
|  | 0-24/120 | 0 | 70 ± 16 | 5 |
|  |  | 100 | 30 ± 2 | 3 |
| Aminopterin | 0-24/120 | 0 | 6.1 ± 1.3 | 2 |
|  |  | 100 | 3.7 ± 0.3 | 2 |

EXAMPLE 2

This example provides data which indicates Thymidylate synthase (TMPS) inhibition is not sufficient to initiate/sustain potentiation of [$^3$H]LV influx by Z. Data in Example 1 show that DHFR inhibition is sufficient for Z potentiation of influx to occur, but not whether DHFR inhibition is necessary. Because MTX acts by indirectly inhibiting two key folate-dependent pathways, thymidylate synthesis and purine synthesis, the effects on potentiation by Z of inhibitors of two enzymes in these pathways, thymidylate synthase (TMPS) and GAR formyltransferase (GARFT), were evaluated. Pre-incubation of CCRF-CEM cells for 10 min with AG337, a specific, lipophilic inhibitor of folate-dependent TMPS, at 2 or 20 µM ($EC_{50}$ for growth inhibition, 0.6 µM) does not potentiate uptake of [$^3$H]LV in the presence or absence of Z. Thus TMPS inhibition is not sufficient to induce Z potentiation of influx. AG337 (20 µM) can, however, completely block the large potentiation of LV uptake induced by TMTX+ Z, as well as the minor increase in uptake seen in the presence of TMTX alone; this antagonism of DHFR inhibition by a TMPS inhibitor is reminiscent of that observed with MTX and 5-FUdR by Moran and co-workers.

EXAMPLE 3

This example provides data which indicates GARFT inhibition is not sufficient to initiate/sustain potentiation of antifolate influx by Z. Since no well-characterized, specific, lipophilic inhibitor of purine synthesis is currently available, an alternate approach was employed utilizing [$^3$H]DDATHF, a specific antifolate GARFT inhibitor that uses the RFC. If de novo purine synthesis inhibition initiates potentiation by Z, DDATHF uptake should be potentiated in the presence of Z after a lag period. We tested the effect of Z on accumulation of DDATHF polyglutamates after a 4 hr incubation with 1 µM [$^3$H]DDATHF, in addition to the 30 min incubation already tested where no effect of Z was observed. This allowed a robust test of whether GARFT inhibition can initiate Z potentiation. In average values from two independent experiments (Table 6), the presence of Z increased the total drug accumulation by only 11%, compared to 300% for MTX. Each DDATHF species was increased by a small amount, although the ranges ±Z overlapped in most cases. Thus, there is at most a very small effect of Z on total DDATHF and DDATHF polyglutamate accumulation over 4 hr. Under both conditions there is extensive DDATHF polyglutamate synthesis, however, which would inhibit GARFT completely, and thus these data strengthen the conclusion that inhibition of purine synthesis is not sufficient to initiate potentiation by Z.

was no different in the absence or presence of 50 µM Z during 120 hr continuous exposure (18.3±3.4 nM vs. 19.8±3.3 nM), 0-16 hr pulse exposure out of 120 hr (85.5±6.5 nM vs. 102.5±17.5 nM), and 0-6 hr pulse exposure out of 120 hr (300±10 nM vs. 320±30 nM). Slopes of the concentration-response curves for pemetrexed were also not altered, unlike those for MTX. Since the primary target of pemetrexed is TMPS, these data are consistent with TMPS inhibition not being sufficient to induce potentiation by Z and thus complement the previous data showing that the lipophilic TMPS inhibitor AG337 cannot induce potentiation by Z. Taken together, the data on DDATHF and pemetrexed further support the suggestion that DHFR inhibition is essential for Z potentiation.

EXAMPLE 5

Z uptake is required for acute potentiation of [$^3$H]MTX uptake. Two approaches were used to test whether transport of Z is required before potentiation of [$^3$H]MTX uptake occurs. Z potentiation was evaluated: (1) in a subline of CCRF-CEM (araC 8C) deficient in the es (or ENT1) facilitated diffusion nucleoside transport system (this is the only nucleoside transporter present in CCRF-CEM cells); and (2) in the presence of specific inhibitors of the es nucleoside transporter. Over a 30 min [$^3$H]MTX uptake time course, the araC 8C subline showed the same uptake kinetics ±Z (i.e., no potentiation ±Z) while parental CCRF-CEM did show potentiation. Data on the effects of the es transporter inhibitors nitrobenzylthioinosine (NBTI or NBMPR), dipyridamole (DP), and dilazep on Z potentiation of 2 µM [$^3$H]MTX uptake were obtained in duplicate studies (Table 7). Note that potentiation by Z is large in these studies because they were performed in HBSS to avoid binding of inhibitors by serum proteins and Z potentiation is higher in HBSS than in RPMI1640. The effects of these inhibitors are compared on only the Z-potentiated portion of [$^3$H]MTX uptake and accumulation ("Relative Corrected" values). NBTI inhibits potentiation by 500 µM Z of $v_i$ and accumulation with an $IC_{50}$ ≈0.1 µM. DP at 10 µM inhibits both $v_i$ and accumulation by 100% so its $IC_{50}$ is <<10 µM; this concentration of DP also affected (30% decrease) [$^3$H]MTX uptake in the absence of Z (it is not clear whether this has been previously reported). Dilazep is not as potent as DP, but its $IC_{50}$ is still <10 µM. All values in the range of those expected for inhibition of es; competition by the high (500 µM) levels of Z might decrease their apparent potency. Thus these data provide strong evidence that Z must be transported before it potentiates [$^3$H]MTX uptake and that Z can be transported by the es nucleoside transport system. Concentration-dependence studies are proposed to quantitate the potency of each inhibitor ($IC_{50}$).

TABLE 6

Effect of Z on accumulation of DDATHF-$Glu_n$

| | DDATHF-$Glu_n$ (pmol/$10^7$ cells) | | | | | | | |
|---|---|---|---|---|---|---|---|---|
| Condition | N = 1 | 2 | 3 | 4 | 5 | 6 | Total N ≥ 3 | Total |
| −Z | 14.8 ± 0.8 | 4.9 ± 0.8 | 9.2 ± 0.9 | 13.3 ± 2.1 | 28.1 ± 2.1 | 30.5 ± 0.9 | 81.1 | 100.8 |
| +Z | 17.5 ± 1.3 | 5.9 ± 0.1 | 10.1 ± 0.1 | 15.2 ± 0.8 | 29.8 ± 0.3 | 33.0 ± 2.3 | 88.0 | 111.3 |

EXAMPLE 4

This example provides data which indicates Z does not increase the growth inhibitory potency of pemetrexed in pulse exposure. Z increases the inhibitory potency of MTX and AMT in pulse, but in continuous, exposure, there is little or no exposure. The effect of 50 µM Z on growth inhibitory potency of pemetrexed (ALIMTA), a multi-targeted antifolate that primarily inhibits TMPS, was similarly assessed in continuous and pulse exposure. The potency of pemetrexed ($EC_{50}$)

TABLE 7

Inhibition of potentiation of [³H]MTX uptake by NBTI, DP, and Dilazep

| [Z], µM | Inhibitor | [I], µM | $v_i$ (pmol/min) | Corrected $v_i$* | Relative Corrected $v_i$** | Accumulation at 30 min (pmol) | Corrected 30 min accumulation† | Rel Corrected 30 min accumulation†† |
|---|---|---|---|---|---|---|---|---|
| — | — | — | 1.4 | — | — | 17 | — | — |
| — | NBTI | 0.1 | 1.4 | — | — | 15.9 | — | — |
| — | NBTI | 1.0 | 1.3 | — | — | 16.4 | — | — |
| — | DP | 10 | 0.95 | — | — | 17.7 | — | — |
| — | Dilazep | 10 | 1.35 | — | — | 18.3 | — | — |
| 500 | — | — | 5.65 | 4.25 | 1 | 108.3 | 91.3 | 1 |
| 500 | NBTI | 0.1 | 3.35 | 1.95 | 0.46 | 70.3 | 54.4 | 0.60 |
| 500 | NBTI | 1.0 | 2.3 | 1.0 | 0.24 | 49.3 | 32.9 | 0.36 |
| 500 | DP | 10 | 0.85 | [−0.1] | [−0.02] | 18.6 | 0.9 | 0.01 |
| 500 | Dilazep | 10 | 1.8 | 0.45 | 0.11 | 34.5 | 16.25 | 0.18 |

*(Rate in presence of Z) − (rate in absence of Z with same inhibitor). Note that this uses slightly different control for each calculation
**Relative to corrected value for +Z but no inhibitor.
†(Accum +Z) − (accum −Z with same inhibitor). Note that this uses slightly different control for each calculation
††Relative to corrected value for +Z but no inhibitor.

EXAMPLE 6

Z metabolism by deoxycytidine kinase is not essential for Z potentiation. These experiments were conducted to determine if Z itself can cause potentiation orf needs to be metabolized to exert its effect. For these experiments, a deoxycytidine kinase (dCK)-deficient subline of CCRF-CEM was used. Although designated as dCK, this enzyme also phosphorylates the purines deoxyadenosine, deoxyguanosine, and fludarabine. Use of this subline allowed us to test the hypothesis that phosphorylation of Z to ZMP by dCK is essential for potentiation. The dCK-deficient subline showed potentiation by Z, although to a slightly lower level compared to that in parental CCRF-CEM. Thus it appears that dCK is not absolutely required for Z potentiation, but may contribute to the metabolism.

EXAMPLE 7

Allantoin, a Z-related compound, does not potentiate [³H] MTX uptake. Recombinant urate oxidase (rasburicase) is approved in the U.S. as an alternative to allopurinol to prevent complications in pediatric malignancies from acute tumor lysis syndrome by converting relatively insoluble uric acid to 100-fold more soluble allantoin (ALN). ALN at 500 µM does not potentiate [³H]MTX uptake in CCRF-CEM cells and up to 100 µM ALN does not inhibit potentiation by 500 µM Z. Based on this result and earlier data, potentiation appears to be specific for Z.

EXAMPLE 8

An inhibitor of protein phosphorylation abrogates the acute Z-induced potentiation of [³H]MTX influx. To determine whether protein phosphorylation is involved in the mechanism of Z potentiation, we began studies with a series of protein kinase (PK) inhibitors (PKI). The initial experiments utilized the PKIs staurosporine and quercetin, and used HEPES-buffered salts solution to avoid protein binding of inhibitors by serum in our standard transport medium. CCRF-CEM cells were incubated for 30 min with PKI and then with TMTX±Z for 10 min, before [³H]MTX was added and 0-30 min uptake was measured. Staurosporine at 10 µM inhibited 30 min accumulation +TMTX by 15% and +TMTX+Z by 8%, thus no specific inhibition was observed in the presence of Z. Quercetin at 50 or 100 µM increased uptake +TMTX at 30 min by 10-12%. Quercetin at 50 µM and 100 µM decreased 30 min accumulation +TMTX+Z by 21% and 38%, respectively. Decreases in initial velocity of uptake were more pronounced; 50 and 100 µM quercetin decreased initial influx rates by 43% and 55%, respectively. The data suggest that protein phosphorylation is involved in Z potentiation. Because quercetin inhibits AMP-activated protein kinase (AMPK), which is typically activated by Z, it supports the hypothesis that AMPK plays a role in Z potentiation.

EXAMPLE 9

An activator of PKA does not acutely potentiate [³H]MTX influx. CCRF-CEM cells incubated for 30 min with 1 mM dibutyryl-cAMP (in the presence of the lipophilic DHFR inhibitor trimetrexate, but the absence of Z) before [³H]MTX was added showed a reduced initial velocity and lower 30 min accumulation compared to cells treated with TMTX alone (and thus much below cells treated with TMTX+Z). Thus PKA is not involved in the acute potentiation caused by Z.

While this invention has been described through the examples presented herein, minor modifications to the various embodiments described herein will be apparent to those skilled in the art and such modifications are intended to be within the scope of the present invention.

REFERENCES

1. Shane, B. Folylpolyglutamate synthesis and role in the regulation of one-carbon metabolism. Vitamins and Hormones, 45: 263-335, 1989
2. Matherly, L. H. and Goldman, D. I. Membrane transport of folates. Vitam Horm, 66: 403-456, 2003
3. Whetstine, J. R., Flatley, R. M., and Matherly, L. H. The human reduced folate carrier gene is ubiquitously and differentially expressed in normal human tissues: identification of seven non-coding exons and characterization of a novel promoter. Biochem J, 367: 629-640, 2002
4. Weitman, S. D., Lark, R. H., Coney, L. R., Fort, D. W., Frasca, V., Zurawski, V. R., Jr., and Kamen, B. A. Distribution of the folate receptor GP38 in normal and malignant cell lines and tissues. Cancer Res., 52: 3396-3401, 1992
5. Jansen, G., Westerhof, G. R., and Jarmuszewski, M. J. Methotrexate transport in variant human CCRF-CEM leukemia cells with elevated levels of the reduced folate carrier. Selective defect on carrier-mediated transport of physiological concentrations of reduced folates. J. Biol. Chem., 265: 18272-18277, 1990
6. Whetstine, J. R., Witt, T. L., and Matherly, L. H. The human reduced folate carrier gene is regulated by the AP2 and sp1 transcription factor families and a functional 61-base pair polymorphism. J Biol Chem, 277: 43873-43880, 2002
7. McGuire, J. J. Anticancer antifolates: Current status and future directions. Curr. Pharmaceutical Design, 9: 2593-2613, 2003
8. McGuire, J. J., Balinska, M., and Russell, C. A. Human cytosolic and mitochondrial folylpolyglutamate synthetase are electrophoretically distinct: expression in antifolate-sensitive and -resistant human cell lines. J. Biol. Chem., 275: 13012-13016, 2000
9. McGuire, J. J. and Russell, C. A. Folylpolyglutamate synthetase expression in antifolate-sensitive and -resistant human cell lines. Oncology Res., 10: 193-200, 1998
10. Foley, G. F., Lazarus, H., Farber, S., Uzman, B. G., Boone, B. A., and McCarthy, R. E. Continuous culture of lymphoblasts from peripheral blood of a child with acute leukemia. Cancer, 18: 522-529, 1965
11. McCloskey, D. E., McGuire, J. J., Russell, C. A., Rowan, B. G., Bertino, J. R., Pizzorno, G., and Mini, E. Decreased folylpolyglutamate synthetase activity as a mechanism of methotrexate resistance in CCRF-CEM human leukemia sublines. J. Biol. Chem., 266: 6181-6187, 1991
12. Rosowsky, A., Lazarus, H., Yuan, G. C., Beltz, W. R., Mangini, L., Abelson, H. T., Modest, E. J., and Frei, E., III Effects of methotrexate esters and other lipophilic antifolates on methotrexate-resistant human leukemic lymphoblasts. Biochem. Pharmacol., 29: 648-652, 1980
13. Nimec, Z. and Galivan, J. Regulatory aspects of the glutamylation of methotrexate in cultured hepatoma cells. Arch. Biochem. Biophys., 226: 671-680, 1983
14. McGuire, J. J., Haile, W. H., and Coward, J. K. Interaction of erythro- and threo-γ-fluoromethotrexate with human leukemia cell dihydrofolate reductase. Biochem. Pharmacol., 38: 4321-4325, 1989
15. Jansen, G., Schomagel, J., Westerhof, G. R., Rijksen, G., Newell, D. R., and Jackman, A. Multiple membrane transport systems for the uptake of folate-based thymidylate synthase inhibitors. Cancer Res., 50: 7544-7548, 1990

What is claimed is:

1. A method for potentiating the uptake and efficacy of an antifolate which acts via inhibition of dihydrofolate reductase (DHFR) on the inhibition of growth of cells in an individual, wherein the individual has a condition selected from the group consisting of cancer, rheumatoid arthritis and psoriasis, comprising administering to the individual an effective amount of a potentiating agent selected from the group consisting of 5-amino-4-imidazolecarboxamide, 5-amino-4-imidazolecarboxamide riboside or a combination thereof and the antifolate at a concentration at which the antifolate inhibits DHFR such that the cells are simultaneously exposed to the antifolate and the potentiating agent and whereby the uptake of the antifolate into the cells and the efficacy of the antifolate is enhanced.

2. The method of claim 1, wherein the antifolate is selected from the group consisting of methotrexate; aminopterin; 10-ethyl-10-deaza-aminopterin; 10-propargyl-10-deazaaminopterin; gamma-methylene-glutamate 10-deaza-aminopterin; talotrexin; and gamma-methylene-glutamate 5,8,10-trideazaaminopterin.

3. The method of claim 2, wherein the antifolate is methotrexate.

4. The method of claim 2, wherein the antifolate is aminopterin.

5. The method of claim 1, wherein the potentiating agent is administered by a method selected from the group consisting of intravenous, intramuscular, intradermal, intratumoral, mucosal, topical and oral.

6. The method of claim 5, wherein the potentiating agent is administered intravenously.

7. The method of claim 6, wherein the potentiating agent is administered over a period from 1 hour to 36 hours.

8. The method of claim 7, wherein the potentiating agent is administered for about 24 hours.

9. The method of claim 7, wherein the potentiating agent is administered sequentially or concurrently with the antifolate.

10. The method of claim 9, wherein the potentiating agent is administered concurrently with the antifolate.

11. The method of claim 1 further comprising administration of a second antifolate to the individual, wherein the second antifolate does not act via inhibition of DHFR.

12. The method of claim 11, wherein the second antifolate is an inhibitor of thymidylate synthase, purine synthase or is a multi-target inhibitor.

13. The method of claim 12, wherein the second antifolate is an inhibitor of thymidylate synthase.

14. The method of claim 12, wherein the second antifolate is an inhibitor of purine synthesis.

15. The method of claim 12, wherein the second antifolate is pemetrexed.

16. The method of claim 1, wherein the individual has acute lymphoblastic leukemia.

17. The method of claim 1, wherein accumulation of polyglutamated form of the antifolate is observed in the cells.

* * * * *